United States Patent [19]
Smith et al.

[11] Patent Number: 5,728,855
[45] Date of Patent: Mar. 17, 1998

[54] MODIFIED POLYALKYLALUMINOXANE COMPOSITION FORMED USING REAGENT CONTAINING CARBON-OXYGEN DOUBLE BOND

[75] Inventors: Gregory M. Smith, Danbury, Conn.; Dennis B. Malpass, La Porte, Tex.

[73] Assignee: Akzo Nobel NV, Arnhem, Netherlands

[21] Appl. No.: 651,290

[22] Filed: May 22, 1996

Related U.S. Application Data

[63] Continuation-in-part of Ser. No. 545,078, Oct. 19, 1995, abandoned.

[51] Int. Cl.$^6$ .................. C07F 5/06; B01J 31/00
[52] U.S. Cl. .............. 556/179; 556/180; 556/187; 502/103; 502/117; 502/152; 526/160; 526/943
[58] Field of Search ................. 556/179, 180, 556/187; 502/103, 117, 152; 526/160, 943

[56] References Cited

U.S. PATENT DOCUMENTS

| | | | |
|---|---|---|---|
| 2,827,458 | 3/1958 | Mirviss et al. | 260/540 |
| 3,168,570 | 2/1965 | Marshall | 260/593 |
| 3,629,216 | 12/1971 | Iwasaki et al. | 260/88.2 |
| 3,969,332 | 7/1976 | Gloriod et al. | 526/128 |
| 4,875,941 | 10/1989 | Piotrowski et al. | 134/11 |
| 5,329,032 | 7/1994 | Tran et al. | 556/179 |
| 5,391,793 | 2/1995 | Marks et al. | 556/179 |

FOREIGN PATENT DOCUMENTS

| | | |
|---|---|---|
| 149949 | 9/1983 | Japan . |
| 271295 | 12/1991 | Japan . |
| 49293 | 2/1992 | Japan . |

OTHER PUBLICATIONS

Chemical Abstracts (1960), 22334b.
Chemical Abstracts (1959), 2093e.
Organoaluminum Compounds, by T. Mole et al., 1972, Elsevier Publishing, pp. 306–307 and 340–343.
E.A. Jeffery et al., "Hemi–Alkoxides from Reactions of Trimethylaluminum with Aldehydes or Ketones", Australian Journal of Chemistry, 1970, 23, 715–724.
S. Pasynkiewicz, "Alumoxanes: Synthesis, Structures, Complexes and Reactions", Polyhedron, vol. 9, No. 23, pp. 429–453.
Comprehensive Organometallic Chemistry: The Synthesis, Reactions and Structures of Organometallic Compounds, G. Wilkinson, ed., vol. 7, pp. 393 and 455 (1982).

*Primary Examiner*—Porfirio Nazario-Gonzalez
*Attorney, Agent, or Firm*—Richard P. Fennelly; Louis A. Morris

[57] ABSTRACT

The present invention relates to a process for forming a composition comprising oligomeric alkylaluminoxane, e.g., preferably methylaluminoxane, and moieties having the structure —$OC(R)_3$, where R is, for example, methyl, which comprises initially treating a composition comprising trialkylaluminum with a reagent containing a carbon-oxygen double bond, such as, carbon dioxide, followed by hydrolysis of the resulting composition with water.

Another embodiment of the invention a composition comprising oligomeric methylaluminoxane and greater than 10 mole % of moieties of the structure —$OC(R)_3$, where R is methyl, which, when such composition is hydrolyzed, there is an evolution of hydrolysis products of methane and at least one $C_2$ or higher alkane, such as t-butane.

27 Claims, No Drawings

MODIFIED POLYALKYLALUMINOXANE COMPOSITION FORMED USING REAGENT CONTAINING CARBON-OXYGEN DOUBLE BOND

This is a continuation-in-part of U.S. Ser. No. 08/545, 078, filed Oct. 19, 1995, now abandoned.

BACKGROUND OF THE INVENTION

The present invention relates to a novel synthesis of aluminoxanes and novel aluminoxane compositions. Aluminoxanes are well known as components for olefin polymerization catalysts.

Aluminoxane compounds are chemical species that incorporate Al—O—Al moieties. While a wide range of aluminoxane species are known their exact structures are not precisely known. The following structures (where R is alkyl and X is an integer of from about 1 to about 40) have been depicted:

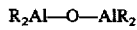

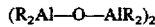

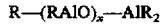

Cyclic and cage cluster structures have also been proposed. Such materials, as would be recognized by the person of ordinary skill in the art are complex mixtures of various species which can easily undergo dynamic exchange reactions and structural rearrangements. A recent review of these materials was authored by S. Pasynkiewicz and appears in Polyhedron, Vol. 9, pp. 429-453 (1990).

Polymethylaluminoxanes (PMAOs), for example, are well known materials with wide utility in olefin polymerization using single-site, or metallocene-based, polymerization catalyst systems (See, for example, Col. 1, lines 14–29 of U.S. Pat. No. 4,960,878 to C. C. Crapo et al.). PMAOs are prepared by controlled hydrolysis of trimethylaluminum (TMAL). Generally, hydrolysis occurs with some loss of aluminum to insoluble species. Generally, PMAOs also have very low solubility in aliphatic solvents, which limits their utility, as well as poor storage stability for solutions containing them. (See, for example, Col. 1, lines 30–46 of U.S. Pat. No. 4,960,878). Finally, it is generally polymethylaluminoxanes that have been the most useful products of this general class of material; other alkylaluminoxanes do not work as well. Since TMAL is an expensive starting material, the resulting PMAO is expensive.

The problems of low yield, poor solubility, poor storage stability, and expensive reagents in preparation of PMAO have previously been attacked, with only limited success, in several ways. One method was to make predominantly PMAO, but include some components from hydrolysis of other aluminum alkyls, to form the so-called "modified methylaluminoxane" (MMAO). This yields predominantly methyl-containing aluminoxanes in improved yields, with improved solution storage stability as well as improved solubility in aliphatic solvents, at lower cost. However, since alkyl groups other than methyl are present, these materials are not always as effective as conventional PMAO.

The prior art contains certain disclosures germane to the composition derived from the instant invention. for example, Japanese Patent publication No. 271295/1991 discloses the reaction of TMAL with t-butanol, followed by reaction with water, at a molar ratio (t-BuOH:Al) of 0.27:1 in Example 1 to yield an aluminoxane product having utility as a co-catalyst. U.S. Pat. No. 5,329,032 to N. H. Tran illustrates, in Col. 7, the addition of various heteroatom-containing reagents, such as esters, ketones, aldehydes, acids, and alcohols, including t-butanol, as solution stabilizer additives to a toluene solution containing PMAO, with a generic description of using such solution stabilizer additives at from 0.1 mole % to 10 mole % (at Col. 3, lines 25–27). For the purposes of this invention, "mole %" should be understood to mean the ratio of moles of additive or reagent to moles of aluminum multiplied by 100. The aluminoxane composition formed by such processes would contain alkoxide (R—O—Al) moieties.

The prior art also contains a number of disclosures relevant to the process of the present invention. Comprehensive Organometallic Chemistry, Vol. 7, p. 393 (in Sec. 46.2.8) mentions the reaction of "triorganoaluminum compounds" with carbon dioxide to "form the corresponding aluminum tricarboxylate", citing earlier work by Ziegler in Justus Liebigs Ann. Chem., 1960, 629, 251, which only shows the use of trialkylaluminum reagents containing two or more carbon atoms in their alkyl groups. Later in that same section, it is stated "Conditions where unreacted trialkylaluminum contacts the dialkylaluminum carboxylate can lead to a trialkylcarbinol" citing its depicted generic formula 69. In addition to the foregoing disclosure, U.S. Pat. No. 2,827,458 to S. B. Mirviss illustrates a process in which an aluminum trialkyl, such as aluminum trihexyl or aluminum triethyl, is reacted with carbon dioxide to yield the corresponding "aluminum salt of the acid" which is then hydrolyzed to form an acid, and U.S. Pat. No. 3,168,570 to D. W. Marshall which described the manufacture of ketones from aluminum trialkyls containing from 2 to 30 carbon atoms in their alkyl groups and carbon dioxide.

SUMMARY OF THE INVENTION

The present invention, in one embodiment, relates to a process for forming a composition comprising oligomeric alkyl-aluminoxane and moieties having the structure —OC(R)$_3$, where R, which can be the same or different, is hydrocarbyl, such as lower alkyl, such as methyl. This process comprises initially treating a composition comprising trialkylaluminum with a reagent containing a carbon-oxygen double bond, such a carbon dioxide, followed by hydrolysis of the resulting composition with water. The —OC(R$_3$) moiety comprises components derived from both the trialkylaluminum and the reagent containing the carbon-oxygen double bond. This —OC(R$_3$) moiety will be further defined below.

Another embodiment of the invention is a composition comprising oligomeric alkylaluminoxane and greater than 10 mole % of moieties of the structure —OC(R)$_3$, where R is a hydrocarbyl group, such as lower alkyl (e.g., methyl), which, when such composition is hydrolyzed, produces an evolution of hydrolysis products, such as methane and at least one C$_2$ or higher alkane, such as isobutane.

DESCRIPTION OF PREFERRED EMBODIMENTS

While broader aspects of the process of the present invention relate to use of a trialkylaluminum reagent or even triaryl or alkyl-aryl aluminum reagents, it is preferred to utilize trimethylaluminum as the organoaluminum compound in such a process. Hence, the remaining discussion will focus on such a preferred embodiment, although it is to be understood that the process claims contained herein are not so limited.

As just mentioned, a preferred embodiment of the present invention relates to a process for forming a composition comprising oligomeric methylaluminoxane and moieties having the structure —OC(R)$_3$, where R is methyl or a mixture of methyl and hydrocarbyl, where the hydrocarbyl groups are derived from the reagent containing a carbon-oxygen double bond, which comprises initially treating a composition comprising trimethylaluminum, in an appropriate organic solvent (aliphatic and/or aromatic, as known to the person of ordinary skill in the art), or in the absence of solvent, with a reagent containing a carbon-oxygen double bond, such as carbon dioxide, followed by hydrolysis to ultimately form a composition comprising oligomeric methylaluminoxane and moieties having the structure —OC(R)$_3$, as earlier defined.

The type of reagents containing the carbon-oxygen double bond can be exemplified by (but not limited to): (1) carbon dioxide, the preferred reagent; (2) ketones; (3) aldehydes; (4) carboxylic acids; (5) carboxylic acid esters; (6) carboxylic acid anhydrides; and (7) carboxylic acid amides. The use of other reagents containing carbon-oxygen double bonds is also within the contemplation of the present invention. When any of reagents (2)–(7), which contain a carbonyl moiety (C=O) as the carbon-oxygen double bond, are chosen they may contain hydrocarbyl moieties selected from either aryl or alkyl moieties, with lower alkyl moieties being preferred. The following Table illustrates, for each of the reagents named above the type of product that is believed to be formed initially and after hydrolysis. Other products may be formed as well, but will not interfere with the ultimate utility of the compositions:

| Reagent | Initial Product | Hydrolysis Product |
|---|---|---|
| Carbon Dioxide | (R$_3$CO)$_x$AlO$_x$R$_{3-3x}$ | (R$_3$CO)$_x$AlO$_{x+y}$R$_{3-3x-2y}$ |
| Ketone | (R'$_2$RCO)$_x$AlR$_{3-x}$ | (R'$_2$RCO)$_x$AlO$_y$R$_{3-x-2y}$ |
| Aldehyde | (R'HRCO)$_x$AlR$_{3-x}$ | (R'HRCO)$_x$AlO$_y$R$_{3-x-2y}$ |
| Carboxylic Acid | (R'R$_2$CO)$_x$AlO$_x$R$_{3-3x}$ | (R'R$_2$CO)$_x$AlO$_{x+y}$R$_{3-3x-2y}$ |
| Esters | (R"O)$_x$(R'R$_2$CO)$_x$AlR$_{3-2x}$ | (R"O)$_x$(R'R$_2$CO)$_x$AlO$_y$R$_{3-2x-2y}$ |
| Anhydrides | (R'R$_2$CO)$_{2x}$AlO$_x$R$_{3-4x}$ | (R'R$_2$CO)$_{2x}$AlO$_{x+y}$R$_{3-4x-2y}$ |
| Amides | (R"$_2$N)$_x$(R'R$_2$CO)$_x$AlR$_{3-2x}$ | (R"$_2$N)$_x$(R'R$_2$CO)$_x$AlO$_y$R$_{3-2x-2y}$ |

The Table given above illustrates how the —OCR$_3$ moieties of the present invention contain both alkyl groups, derived from the trialkylaluminum and hydrocarbyl groups, derived from the reagent containing the carbon-oxygen double bond.

The composition resulting from the treatment of trimethyl-aluminum with carbon dioxide, for example, as the reagent containing the carbon-oxygen double bond, comprises aluminoxane and alkoxide containing compositions, which may be approximately represented by the formulae Me$_2$AlOAlMe$_2$ and Me$_2$AlOC(Me)$_3$, where Me is methyl. The composition comprising the preferred trimethylaluminum reagent, which is preferably to be treated with carbon dioxide, also can comprise one or more hydrocarbylaluminum compounds, e.g., one or more trialkylaluminum compounds, containing alkyl groups having two or more carbon atoms if the so-called "modified methylaluminoxane"-type compositions are desired.

Another embodiment of the invention is a novel composition comprising oligomeric methylaluminoxane and greater than 10 mole of moieties of the structure —OC(R)$_3$, as earlier defined, which, when such composition is hydrolyzed, produces hydrolysis products comprising methane and, for example, at least one C$_2$ or higher alkane, such as isobutane. This relates to the so-called "modified methylaluminoxane"-type compositions as contrasted to conventional methylaluminoxane compositions.

The present invention is most useful where an improved composition or process for a methylaluminoxane is needed, and the methylaluminum portion of the composition must remain relatively unmodified. The invention leaves the methylaluminum component (derived from the TMAL reagent) relatively unmodified, unless a higher alkyl group-containing hydrocarbylaluminum reagent is also used. TMAL, when reacted with the preferred carbon dioxide (CO$_2$) reagent, prior to hydrolysis, forms both aluminoxane groups and t-butoxide groups. A possible, non-limiting reaction equation showing the formation of what are believed to be the most likely, predominant species of the preferred reaction is as follows:

$$3\ Me_3Al + CO_2 \rightarrow Me_2AlOAlMe_2 + Me_2AlOC(Me)_3$$

Using CO$_2$ to introduce —OCR$_3$ moieties has the advantages of being easy and inexpensive, while simultaneously forming some of the desired aluminoxane product, thereby further reducing the amount of water required for hydrolysis.

Once some aluminum alkoxide is introduced, for example, by treatment of TMAL with carbon dioxide, which results in simultaneous formation of aluminoxane and t-butoxide groups, this intermediate composition can be partially hydrolyzed (forming additional aluminoxane). Because of the prior introduction of aluminoxane and/or alkoxide moieties, the amount of water required for hydrolysis to catalytically useful aluminoxane compositions is reduced. This results in improved recovery of soluble aluminum, while still yielding good polymerization activity.

Other advantages of this invention include improved solubility, or storage stability, or both, for the aluminoxane product formed.

If desired, supported polyalkylaluminoxane compositions can be prepared by conducting the aforementioned reaction in the presence of a suitable support material. Alternatively, supported alkylaluminoxanes may also be prepared by forming the alkylaluminoxanes of this invention in a discrete, separate step and subsequently allowing the alkylaluminoxane to react with the support material. Oxidic support materials, such as silica, are especially preferred.

As will be appreciated by the person of ordinary skill in the art, the aluminoxane products that can be made by the process of the present invention are useful as cocatalysts in those single-site (metallocene-based) catalyst systems which are useful in the polymerization of olefin monomers in a manner analogous to that in current use with the aluminoxane compositions that are currently known and used in that manner.

EXAMPLES 1–6

Standard air-free glove box and Schlenk line techniques were used in these Examples. The trimethylaluminum (TMAL) that was utilized contained 36.9 wt % aluminum.

Four samples of 5.00 g, each, of TMAL were charged into separate 130 mL septum sealed glass vials. Each neat sample was treated with the amount of CO$_2$ gas indicated in Table 1:

TABLE 1

| Sample | TMAL (gm) | CO₂ (gm) | CO₂/Al |
|---|---|---|---|
| A | 5.00 | 0.00 | 0.00 |
| B | 5.00 | 0.50 | 0.17 |
| C | 5.00 | 1.03 | 0.34 |
| D | 5.00 | 1.20 | 0.40 |
| E | 5.00 | 0.00 | 0.00 |
| F | 5.00 | 0.00 | 0.00 |

Each sample was then combined with toluene and hydrolyzed with water, using the amounts shown in Table 2, below. Hydrolysis was performed by the slow dropwise addition of water to the chilled (−50° to −80° C.) toluene solutions of the metal alkyls. Slow warming to room temperature, between additions of small aliquots of water, was used to control the hydrolysis reaction. Solids formed in samples A, B, E and F, but not in samples C and D. Samples C and D were used as is, while samples A, B, E and F were divided into supernatant and slurry by decantation. The aluminum concentration in the clear supernatants (A, B, E, F) or the entire sample (C & D), combined with the total mass (includes slurry) of the samples was used to estimate the recovery of soluble aluminum (also in Table 2) which follows:

TABLE 2

| Sample | CO₂/Al | H₂O(gm) | H₂O/Al | Al (wt %) | Al Recov.(%) |
|---|---|---|---|---|---|
| A | 0.00 | 0.947 | 0.77 | 2.13 | 56% |
| B | 0.17 | 0.572 | 0.47 | 3.03 | 81% |
| C | 0.34 | 0.164 | 0.13 | 3.57 | 97% |
| D | 0.40 | 0.000 | 0.00 | 3.53 | 98% |
| E | 0.00 | 0.624 | 0.51 | 2.90 | 80% |
| F | 0.00 | 1.003 | 0.82 | 2.03 | 56% |

The polymerization activity towards polyethylene (1000 Al/Zr, with rac-ethylenebisindenyl zirconium dichloride: kg PE/gm Zr hr) utilizing the methylaluminoxane materials previously described is shown in Table 3:

TABLE 3

| Sample | CO₂/Al | H₂O/Al | Al Rec.(%) | Activity |
|---|---|---|---|---|
| A | 0.00 | 0.77 | 56 | 380 |
| B | 0.17 | 0.47 | 81 | 610 |
| C | 0.34 | 0.13 | 97 | 76 |
| D | 0.40 | 0.00 | 98 | 32 |
| E | 0.00 | 0.51 | 80 | 390 |
| F | 0.00 | 0.82 | 56 | 430 |

This data demonstrates that at hydrolysis conditions which lead to improved recovery of aluminum (Sample B), good polymerization activity is obtained with the product of this invention.

The ¹H NMR spectrum for TMAL shows a sharp ¹H NMR signal near δ−0.33 ppm. It is well known that conventional polymethylaluminoxane (PMAO) gives a broad ¹H NMR signal (from the aluminoxane species) in the range from about δ0.0 to −0.8 ppm (See, for instance, spectra included in Malpass, D. B. et. al. Modified Methyl Aluminoxanes for Single Site Catalysis, Proceedings of SPO '93, Schotland Business Research Inc., Princeton, N.J. 1993. pp 185-204). A ¹H NMR spectrum of dimethylaluminum t-butoxide demonstrates that t-butoxide groups tend to give sharp signals at about δ1.16 ppm. The spectra for samples B, C and D (after CO₂ addition, but prior to H₂O addition) demonstrated that, as increasing amounts of CO₂ were reacted with TMAL, materials were formed with increasing amounts of broad signals in the PMAO region, decreasing amounts of TMAL signals, and increasing amounts of sharp signals in the t-butoxide regions. Though many species are present due to dynamic interchange reactions characteristic of aluminoxane compositions, this data is consistent with the equation written below, where TMAL is converted into a mixture of aluminoxane and Al—O—t—Bu containing species:

$$3\ Me_3Al + CO_2 \rightarrow Me_2AlOAlMe_2 + Me_2AlOC(Me)_3$$

The foregoing Examples, since they merely illustrate certain embodiments of the present invention, should not be construed in a limiting sense. The scope of protection sought is set forth in the claims which follow.

We claim:

1. A process for forming a composition comprising oligomeric alkylaluminoxane and moieties having the structure —OC(R)₃, where R is either the same or different and is hydrocarbyl, which comprises initially treating a composition comprising trialkylaluminum with a reagent containing a carbon-oxygen double bond at greater than 10 mole %, followed by hydrolysis of the resulting composition.

2. A process as claimed in claim 1 wherein the composition is formed after treatment of trimethylaluminum with carbon dioxide.

3. A process as claimed in claim 1 wherein the composition which is treated with the reagent containing a carbon-oxygen double bond comprises trimethylaluminum and one or more hydrocarbylaluminum compounds containing alkyl groups having two or more carbon atoms.

4. A process as claimed in claim 1 wherein the reagent is carbon dioxide.

5. A process as claimed in claim 1 wherein the reagent containing the carbon-oxygen double bond is a carbonyl compound.

6. A process as claimed in claim 5 wherein the carbonyl compound is selected from the group consisting of a ketone, an aldehyde, a carboxylic acid, a carboxylic acid ester, a carboxylic acid anhydride, and a carboxylic acid amide.

7. A product formed by the process of claim 1.
8. A product formed by the process of claim 2.
9. A product formed by the process of claim 3.
10. A product formed by the process of claim 4.
11. A product formed by the process of claim 5.
12. A product formed by the process of claim 6.

13. A composition comprising oligomeric methylaluminoxane and greater than 10 mole % of moieties of the structure —OC(R)₃, where R is hydrocarbyl, which, when such composition is hydrolyzed, produces hydrolysis products comprising methane and at least one C₂ or higher alkane.

14. A composition as claimed in claim 13 wherein the higher alkane is isobutane.

15. A process for forming a composition comprising oligomeric alkylaluminoxane and moieties having the structure —OC(R)₃, where R is alkyl, which comprises initially treating a composition comprising trialkylaluminum with carbon dioxide, followed by hydrolysis of the resulting composition.

16. A process as claimed in claim 15 wherein the composition which is treated with carbon dioxide comprises trimethylaluminum and one or more hydrocarbylaluminum compounds containing alkyl groups having two or more carbon atoms.

17. The product formed by the process of claim 15.

18. The product formed by the process of claim 16.

19. The supported product formed by the process of claim 1.

20. The supported product formed by the process of claim 2.

21. The supported product formed by the process of claim 2.

22. The silica-supported product formed by the process of claim 1.

23. The silica-supported product formed by the process of claim 2.

24. The silica-supported product formed by the process of claim 3.

25. A catalyst composition for use in the polymerization of olefins which comprise the aluminoxane, optionally on a support, formed by the process of claim 1.

26. A catalyst composition for use in the polymerization of olefins which comprise the aluminoxane, optionally on a support, formed by the process of claim 2.

27. A catalyst composition for use in the polymerization of olefins which comprise the aluminoxane, optionally on a support, formed by the process of claim 3.

* * * * *